United States Patent [19]

Hofmann

[11] Patent Number: 5,004,821

[45] Date of Patent: Apr. 2, 1991

[54] PRODUCTION OF PHENYLARSINES

[75] Inventor: Hartmut Hofmann, Gottingen, Fed. Rep. of Germany

[73] Assignee: PPM Pure Metals GmbH, Langelsheim, Fed. Rep. of Germany

[21] Appl. No.: 456,233

[22] Filed: Dec. 27, 1989

Related U.S. Application Data

[62] Division of Ser. No. 336,415, Apr. 11, 1989, abandoned.

[30] Foreign Application Priority Data

Apr. 13, 1988 [DE] Fed. Rep. of Germany ....... 3812180

[51] Int. Cl.$^5$ .............................................. C07F 9/66
[52] U.S. Cl. ...................................................... 556/70
[58] Field of Search .................. 556/70; 156/610, 611, 156/612, 613, 614, DIG. 73

[56] References Cited

U.S. PATENT DOCUMENTS

| | | | |
|---|---|---|---|
| 4,734,514 | 3/1988 | Hofmann | 568/8 |
| 4,857,655 | 8/1989 | Valentine, Jr. | 556/70 |
| 4,900,855 | 2/1990 | Hui et al. | 556/70 |

OTHER PUBLICATIONS

Chen et al., "MOVPE Growth of InP Using Isobutylphospine and Tertiary Butylphosphine", Journal of Crystal Growth (77), 1986, pp. 11-18.

Chen et al., "Use of Tertiary Butylarsine for GaAs Growth", Applied Physics Lett. 50(4), Jan. 26, 1983, pp. 218-220.

Chen et al., "Organometallic VPE Growth of InP Using Phosphorus Sources", Applied Physics Lett. 48, Jan. 2, 1986 (22), pp. 1531-1533.

Lum et al., "Use of Tert-Butylarsine in MOCVD of GaAs Growth", Applid Physics Letter, 50(5), Feb. 2, 1987, pp. 284-286.

*Primary Examiner*—Arthur C. Prescott
*Attorney, Agent, or Firm*—Lockwood, Alex, FitzGibbon & Cummings

[57] ABSTRACT

Organic metallic compounds in the form of phenylarsines are used in epitaxy processes, such as MO-VPE, MO-CVD or MOMBE processes, as well as for ion implantation or the in-situ doping of polysilicon for semi-conductors.

6 Claims, No Drawings

PRODUCTION OF PHENYLARSINES

This application is a division of application Ser. No. 336,415, filed Apr. 11, 1989, now abandoned.

DESCRIPTION OF THE INVENTION

This invention relates to organic arsenic compounds for the production of layers in gas phase epitaxy processes, particularly for the production of semi-conductors.

In the manufacture of semi-conductors and related components it is desirable and necessary to produce controlled precipitates from specific phosphides, arsenides or trivalent metals, such as for example of gallium, indium or aluminum.

During the early days of gas phase epitaxy, III/V semi-conductors were produced by using arsine, i.e. arsenic hydride $AsH_3$. However, the use of arsine has certain disadvantages. Because of the great toxicity of arsenic hydride, great dangers and risks are present. Also, the purity of the supply containers for this material have played an important role in these processes, as well as the low pyrolysis speeds at the low temperatures of gas phase epitaxy processes. Furthermore, the gaseous nature of the arsenic hydride itself results in certain disadvantages.

It has therefore been attempted to replace the arsenic hydride with for example tertiary butylarsine ($BT_3As$) (Appl. Phys. Lett., vol. 50, no. 4, Jan. 26, 1987), or by metallic alkyls of another type which were produced using metallic halogenides and a Grignard compound (U.S. Pat. No. 4 611 017; U.S. Pat. No. 4 621 147).

It is thus the task of the present invention t utilize organic compounds which are advantageous in both their production and their use. This task is achieved by the phenylarsines in accordance with the present invention.

With the phenylarsines of the present invention it is possible to form films with metallic organic compounds of the III primary group of the periodic system, preferably triethylgallium (TEG) Such films exhibit excellent photoluminescence characteristics at the temperature of 830° K. and V/III ratios of up to 2.3. Such films and their layers also have low compensation $\mu_{77}=2.10^4 cm^2/Vs$, $n_{77}=1.10^{15} cm^{-3}$ and reflecting surfaces.

The processing and production of such epitaxy layers takes place, in accordance with known processes, for example in a reactor under atmospheric pressure and an induction heating system in order to reach epitaxial growth temperatures. The processing of the compounds in accordance with the invention can also be plasma-stimulated or photochemical or can take place by means of thermal disintegration.

The support gas is laden with vaporous phenylarsine. The flow speed and the temperatures in the range of 700 to 900° K. are selected corresponding to epitaxial growth process conditions. The hydrogen flow moves over the substrate during the heating period, whereby the known process takes place.

The preparation of the phenylarsines in the present invention takes place under the exclusion of oxygen and the freedom from oxygen of all solvents and acids. $PhAsH_2$ may be produced in the following manner:

78 g (0.39 mol) of phenylarsonic acid are added with a maximum 160 g (2.45 mol) zinc, preferably as chips or in tablet form, to a flask with a reflux cooler, stirring device and dropping funnel. Both solids are intensively mixed thoroughly with 200 ml of water. 200 ml of donor-free solvent, preferably n-pentane, are added to this so that a phase separation can also take place. During cooling at room temperature and below, 400 ml of conc. hydrochloric acid are added by dropping at a slow rate such that the development of hydrogen can barely be detected.

After all the phenylarsonic acid has been consumed, the organic phase is separated, and the aqueous phase is repeatedly extracted with small portions of solvent. The organic phase, as well as all the extracts, are united and pre-dried with a drying agent, such as for example a molecular sieve. The remaining water traces can be removed by means of a strong drying agent, such as for example phosphorous pentoxide ($P_4O_{10}$). All further operations are now continued with the most rigorous exclusion of water. The solvent is completely separated from the product through condensation or distillation. The remaining phenylarsine can then either be purified through recondensation or through distillation under vacuum to yield about 45 g (45 g corresponds to 76% of the theoretical yield).

Particular reference should be made to the fact that the zinc reducing agent is present in a highly pure state, and must have the form of chips or tablets.

The compounds proposed in accordance the the invention can also be used in the known VO-VPE, MO-CVD or MOMBE processes.

The production process is also possible without the presence of water, since the phenylarsonic acid and the reduction agent are suspended directly in the organic solvent.

What I claim is:

1. A process for the production of a phenylarsine, comprising
   mixing phenylarsonic acid with substantially pure zinc in chip or tablet form in a solvent;
   cooling the mixture while adding substantially pure hydrochloric acid thereto, said hydrochloric acid being added at a slow rate such that the formation of hydrogen is only slight to form the phenylarsine;
   separating and drying the phenylarsine by phase separation and extraction; and
   all of the foregoing steps being performed in the absence of oxygen.

2. The process of claim 1, wherein the solvent is separated from the phenylarsine by condensation or distillation, and the phenylarsine is purified under vacuum by distillation or recondensation.

3. The process of claim 1, wherein said solvent includes an organic solvent which contains said phenylarsine.

4. The process of claim 3, wherein said solvent containing said phenylarsine is dried with a drying agent.

5. The process of claim 2, wherein said solvent containing said phenylarsine is dried with a drying agent.

6. The process of claim 5, wherein said solvent containing said phenylarsine is dried with a drying agent.

* * * * *

UNITED STATES PATENT AND TRADEMARK OFFICE
CERTIFICATE OF CORRECTION

PATENT NO. : 5,004,821

DATED : April 2, 1991

INVENTOR(S) : Hartmut Hofmann

It is certified that error appears in the above-identified patent and that said Letters Patent is hereby corrected as shown below:

In column 1, line 35, delete "t" and insert -- to --.

In column 1, line 43, after "(TEG)" insert a period.

Signed and Sealed this

Eighteenth Day of August, 1992

Attest:

DOUGLAS B. COMER

*Attesting Officer*  *Acting Commissioner of Patents and Trademarks*